United States Patent [19]

Ludwig et al.

[11] 4,331,652

[45] May 25, 1982

[54] CONTROLLED RELEASE PARASITIC FORMULATIONS AND METHOD

[75] Inventors: Nelson H. Ludwig; Rudolph J. Boisvenue, both of Greenfield, Ind.

[73] Assignee: Eli Lilly and Company, Indianapolis, Ind.

[21] Appl. No.: 219,790

[22] Filed: Dec. 24, 1980

Related U.S. Application Data

[63] Continuation-in-part of Ser. No. 74,681, Sep. 12, 1979, abandoned.

[51] Int. Cl.$^3$ ............................ A61K 9/22; A61K 9/26
[52] U.S. Cl. .......................................... 424/19; 424/22
[58] Field of Search .................................... 424/19–22

[56] References Cited

U.S. PATENT DOCUMENTS

| | | | |
|---|---|---|---|
| 3,056,724 | 10/1962 | Marston | 424/22 |
| 3,507,952 | 4/1970 | Rednick | 424/22 |
| 3,535,419 | 10/1970 | Siegrish et al. | 424/22 |
| 3,736,646 | 6/1973 | Schmitt et al. | 29/458 |
| 3,773,919 | 11/1973 | Boswell et al. | 424/19 |
| 3,887,699 | 6/1975 | Yolles | 424/19 |
| 3,972,999 | 8/1976 | Tsuk | 424/78 |
| 3,976,071 | 8/1976 | Sadek | 128/260 |
| 3,991,766 | 11/1976 | Schmitt et al. | 128/335.5 |
| 4,011,312 | 3/1977 | Reuter | 424/78 |
| 4,076,798 | 2/1978 | Casey et al. | 424/22 |
| 4,118,470 | 10/1978 | Casey et al. | 424/19 |
| 4,144,317 | 3/1979 | Higuchi et al. | 424/21 |
| 4,159,322 | 6/1979 | Cloyd | 424/181 |
| 4,166,107 | 8/1979 | Miller et al. | 424/19 |
| 4,166,800 | 9/1979 | Fong | 252/316 |

OTHER PUBLICATIONS

Oklahoma Farmer-Stockman, Dr. Jakie Hair, Feb. 1979, p. 11.

*Primary Examiner*—Shep K. Rose
*Attorney, Agent, or Firm*—Charles W. Ashbrook; Arthur R. Whale

[57] ABSTRACT

Controlled release formulations useful in controlling endoparasitic infestation in animals over a prolonged period of time are comprised of an anthelmintic agent intimately dispersed throughout a copolymeric matrix derived from the condensation of about 60 to about 95 weight percent of lactic acid and about 40 to about 5 weight percent of glycolic acid, said copolymeric matrix being substantially free of polymerization catalyst.

9 Claims, No Drawings

CONTROLLED RELEASE PARASITIC FORMULATIONS AND METHOD

CROSS-REFERENCE TO RELATED APPLICATIONS

This is a continuation-in-part of copending application Ser. No. 74,681, filed Sept. 12, 1979 now abandoned.

BACKGROUND OF THE INVENTION

Parasites constitute a major problem in animal husbandry. Most animals suffer from free-flying parasites such as mosquitos, horn flies and stable flies; crawling ectoparasites such as lice, ticks, fleas and mites, burrowing parasites such as bots and grubs, as well as microscopic endoparasites such as coccidia, worms and the like. Several methods for partial control of such parasites are known. For example, free-flying parasites such as flies can be marginally controlled by standard methods such as air-dispersed and contact insecticides and fly traps. Intestinal parasites are typically controlled by periodic de-worming, for instance by tube worming in the case of equine. Skin-inhabiting and crawlingparasites and usually controlled by drenching, washing, or spraying the animals with appropriate parasiticides. Many of the available treatments require the use of extremely toxic substances, for example organophosphates, and heavy metal preparation such as arsenic and mercury formulations.

A major problem exists in the treatment of parasites in domestic animals which are allowed to roam freely over a specified area. For example, animals such as cattle and sheep, which are raised for their human food and clothing products, are often permitted to feed and grow on open grassland, particularly during warm weather grass growing seasons. Also, because herds of such animals are often rather large, individual treatment at short intervals is economically prohibitive. Consequently, such animals are not subject to normal methods of controlling parasites.

Additionally, many parasites, including mosquitoes, lice, mites and the like, lay eggs on an animal, and the eggs hatch within about twenty one days. The only way to destroy the repeating crops of parasites is to have repeated treatments of spraying or drenching, or alternatively to have a continuous supply of an effective amount of a parasiticide in the blood stream of an animal for a prolonged period following a single administration.

The idea of prolonged release formulations for the continuous delivery of an active agent to an animal system over a predetermined period of time is known. For example, Siegrist et al. in U.S. Pat. No. 3,535,419, disclose sustained release veterinary compositions useful for ruminant fertility control. As pointed out by Siegrist et al., the current state of development of such sustained release formulations suffers in so many respects that widespread use is precluded. In particular, slow release implants suffer from leaving unwanted residues following payout of the active ingredient, as well as failing to afford sufficiently sharp and consistent endpoints to be predictable.

Reuter et al., in U.S. Pat. No. 4,011,312, describe what is said to be a prolonged release drug dosage form useful for the treatment of bovine mastitis. Such formulation comprises an antimicrobial agent dispersed in a matrix of a low molecular weight polyester of glycolic and lactic acids. The polyester utilized is required to contain about 60 to 80 mole percent of glycolic acid and 20 to 40 mole percent of lactic acid, with a molecular weight of less than 2000. Such formulations are said to provide effective medication for up to four to six weeks.

Moreover, many prior art compositions suffer from leaving unwated residues upon dissolution of the copolymer matrix. This is of utmost importance when the compositions are to be used in animals raised for human food production. Moreover, since many chemical compounds which are effective against diseases at certain dose levels can be lethal to the host animal when administered in excessive amounts, it is imperative that a controlled release formulation be one that does not expose the host animal to lethal doses.

An object of the present invention is to provide a unique formulation of a parasiticide combined with a copolymer of lactic acid and glycolic acid such that the active agent is controllably released and total biodegradation of the copolymeric matrix is achieved with no unwanted residue remaining in the animal tissue. A further object is to provide a formulation which is capable of systemically providing uniform protection against endoparasites for a predetermined period of time.

SUMMARY OF THE INVENTION

This invention relates to controlled release anthelmintic formulations and to a method for systemically controlling animal parasites. More particularly, the invention provides a controlled release biodegradable dosage form useful in the treatment and control over a prolonged period of time of internal parasites in domestic animals. The dosage form is comprised of about 20 to about 80 percent by weight of a suitable anthelmintic agent intimately dispersed throughout about 80 to about 20 percent by weight of a copolymeric matrix dervied from about 60 to about 95 weight percent of lactic acid and about 40 to about 5 weight percent of glycolic acid. Such copolymeric matrix has an inherent viscosity when measured in chloroform of about 0.08 to about 0.30, and a molecular weight of about 6000 to about 35000. The copolymer matrix is prepared by a novel process which permits the substantially (ie. greater than about 95 percent) complete removal of toxic catalysts or residues, thus rendering the matrix totally biodegradable into substances common to animal systems. The novel copolymer and the process for its preparation is described in copending application Ser. No. 75,296 filed Sept. 12, 1979, by Robert S. Nevin.

A preferred copolymeric matrix is one derived from about 60 to about 90 weight percent of lactic acid and about 40 to about 10 weight percent glycolic acid with an inherent viscosity of about 0.10 to about 0.25.

A more preferred copolymeric matrix utilized in the formulations of this invention is one derived from about 70 to about 80 weight percent lactic acid and about 30 to about 20 percent glycolic acid, with an inherent viscosity of about 0.13 to about 0.23 and a molecular weight of about 15000 to about 30000.

The anthelmintic agents which can be employed in the formulations of the invention are any of those which are known to be effective for the systemic control of endoparasites which feed on tissues of animals. Typical of those which are comprehended in the controlled release formulations of this invention are the benzimidazole methylcarbamates having the formula

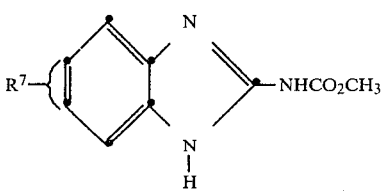

wherein $R^7$ is hydrogen, lower alkyl, lower alkoxy, lower alkylthio, benzoyl, halobenzoyl, phenylthio, phenylsulfinyl, cyclopropylmethylsulfinyl, and lower alkyl—$CO_2NH$. Particularly preferred benzimidazoles having the above formula are methyl-5(6)-phenylthiobenzimidazole carbamate, generically referred to as fenbendazole (U.S. Pat. No. 3,954,791) and methyl 5-propylthio-1H-benzimidazole-2-yl carbamate, generically referred to as albendazole. In the above formula defining benzimidazole methylcarbamates, $R^7$ defines a lower alkyl group such as $C_1$-$C_4$ alkyl, lower alkoxy such as $C_1$-$C_4$ alkoxy, lower alkylthio such as $C_1$-$C_4$ alkylthio, and lower alkyl—$CO_2NH$— such as $C_1$-$C_4$ alkyl—$CO_2NH$.

Compounds closely related to the above-mentioned benzimidazoles which also are comprehended in the formulations of this invention include thiabendazole, which is 2-(4-thiazolyl)benzimidazole; leyamisole, which is 6-aminophenyl-(2,3,5,6)tetrahydroimidazo(2,1-b)thiazole; and febantel, which is N-(2-[2,3-bis-(methoxycarbonyl)guanidino]-5-(phenylthio)phenyl)-2-methoxyacetamide.

U.S. Pat. No. 4,104,400 describes a series of imidazo(2,1-b)thiazoles which are particularly effective in treating or inhibiting helminthiasis, and accordingly can be formulated with a copolymer matrix according to this invention in order to achieve a controlled release form ideally suited to protecting animals for a prolonged period of time following a single administration.

Anthelmintic imidazo[1,2-a]pyridines are disclosed in U.S. Pat. No. 4,154,835. These compounds are also contemplated in the formulations and method provided by this invention.

Still other benzimidazole carbamates which are formulated for controlled release according to this invention are those recited in U.S. Pat. Nos. 4,154,846 and 4,156,006. Both references are incorporated herein by reference.

Additional parasitic agents which are formulated according to this invention include Banminth, which is trans-1,4,5,6-tetrahydro-1-methyl-2-[2-(2-thienyl)vinyl]-pyrimidine hydrogen tartrate, and diamphenethide, which is bis($\beta$-(4-acetamidopheoxy)ethyl)ether.

A further embodiment of this invention is a method for continuously controlling endoparasites in animals over a prolonged period of time which comprises administering to an animal in need of treatment or to an animal exposed to parasites an effective amount of a controlled release formulation of this invention which is comprised of about 20 to about 80 percent by weight of an effective anthelmintic agent intimately dispersed throughout a copolymeric matrix derived from the condensation of about 60 to about 95 weight percent lactic acid and about 40 to about 5 weight percent of glycolic acid. An especially preferred method of treatment comprises administering an effective amount of a formulation containing as active ingredient fenbendazole.

DETAILED DESCRIPTION OF THE INVENTION

This invention provides a controlled release formulation which can be administered therapeutically or prophylactically to an animal suffering from endoparasitic infestation or being prone to development of such parasitic infestation. Such formulation provides effective treatment and control of endoparasitic infestations for a prolonged period of time following a single administration. Periodic administration of the formulation thus provides indefinite protection to animals. Typically, a single administration of a controlled release formulation of this invention provides effective control of parasitic infestation for a period of about ten to about sixty days.

The formulations provided by this invention require a copolymeric material which is uniquely and ideally suited to the controlled release of an effective amount of a pharmaceutical agent to an animal such that the animal can be effectively treated with a minimum of administrations. Such copolymeric material is prepared by a process which permits the substantially complete removal of polymerization catalyst, thereby permitting the total degradation of the copolymeric matrix in a biological system without the concomitant accumulation of toxic residues in animal tissues. This aspect of the invention is of particular significance in the treatment of animals utilized in the production of meat and other animal products intended for human consumption. The new copolymer is described in detail by Nevin in Ser. No. 75,296 filed Sept. 12, 1979.

The copolymers required for the formulations of this invention are prepared by condensation of lactic acid and glycolic acid in the presence of a readily removable polymerization catalyst. Such catalysts include strong acid ion-exchange resins in the form of beads or similarly hard structures which are easily removed by filtration or similar techniques. Particularly preferred polymerization catalysts include commercially available strong acid ion-exchange resins such as Amberlite IR-118(H), Dowex HCR-W (formerly Dowex 50W), Duolite C-20, Amberlyst 15, Dowex MSC-1, Duolite C-25D, Duolite ES-26 and related strong acid ion-exchange resins. The catalyst is added to a mixture of about 60 to about 95 parts by weight of lactic acid and about 40 to about 5 parts by weight of glycolic acid. The amount of catalyst utilized is not critical to the polymerization, but typically is from about 0.01 to about 20.0 parts by weight relative to the total weight of combined lactic acid and glycolic acid. The polymerization generally is carried out in the absence of solvents; however, organic solvents such as dimethylsulfoxide or N,N-dimethylformamide can be utilized if desired. The polymerization reaction routinely is carried out in a reaction system equipped with a condensing system, thereby permitting the collection and removal of water that is formed, as well as facilitating the removal of any lactide and glycolide by-products that are formed. The polymerization reaction generally is conducted at an elevated temperature of about 100° to about 250° C., and at such temperature is usually substantially complete within about 3 to about 172 hours, normally about 48 to about 96 hours. Ideally, the reaction can be carried out under a reduced pressure, thereby further facilitating removal of water and by-products.

The copolymer thus formed is readily recovered by simply filtering the molten reaction mixture, for example through a wire screen, to remove substantially all of the strong acid ion-exchange polymerization catalyst. Alternatively, the reaction mixture can be cooled to room temperature and then dissolved in a suitable organic solvent such as dichloromethane or acetone and then filtered by normal means so as to remove the solvent-insoluble strong acid ion-exchange resin. The copolymer then is isolated by removal of the solvent from the filtrate, for instance by evaporation under reduced pressure. Further purification of the copolymer can be accomplished if desired by redissolving it in a suitable organic solvent and further filtration, including the use of standard filter aids if desired.

The copolymer thus formed is required in the formulations and method of treatment provided by this invention. Such copolymers, while not amenable to exact structure elucidation, are characterized as having a molecular weight of about 6000 to about 35000, and ideally about 15000 to about 30000. The copolymers are unique in that they are classified as high molecular weight substances having an inherent viscosity of about 0.08 to about 0.30 when measured by standard techniques utilizing an Ubbelohde viscometer in which chloroform has an efflux time of about 51 seconds at 25° C. The inherent viscosity of the copolymers is determined by the following equations:

$$\eta r = t/t_o \qquad \eta inh = \frac{\ln \eta r}{C}$$

wherein:
$\eta r$ is relative viscosity;
$t_o$ is efflux time of solvent;
$t$ is efflux time of the solution;
$\eta inh$ is inherent viscosity;
C is concentration in grams per 100 ml. of solvent; and
ln is logarithm.

The copolymers utilized in the formulations of this invention are additionally unique in that they are capable of providing a controlled release of pharmaceutical agents heretofore unavailable in animal tissues.

The formulations comprehended by this invention comprise an effective amount of a pharmacologically active parasitic agent uniformly admixed and dispersed throughout the copolymeric matrix hereinabove described. As used herein, the term "parastic agent" includes any of the well known and commonly used anthelmintic agents. The formulations contain about 20 to about 80 percent by weight of active ingredient, ideally about 30 to about 70 percent. The pharmacologically active agents which can be utilized in the formulations include those agents commonly employed in the control of parasites in animals. Commonly used active agents include the following:

methyl 5-benzoyl-2-benzimidazole carbamate;
methyl 5(6)phenylthio-2-benzimidazole carbamate;
methyl (5-(phenylsulfinyl)-1H-benzimidazol-2-yl)carbamate;
methyl 5[(cyclopropylmethyl)sulfinyl]-1H-benzimidazol-2-yl]carbamate;
methyl 2-benzimidazole carbamate;
methyl 5(6)-butyl-2-benzimidazole carbamate;
methyl 5-propylthio-1H-benzimidazol-2-yl carbamate;
methyl 6-isopropylcarbonyloxyamino-2-benzimidazole carbamate;
methyl 5n-propoxy-2-benzimidazole carbamate;
methyl 5-(4-fluorobenzoyl)-2-benzimidazole carbamate;
methyl 5-isobutylsulfinyl-2-benzimidazole carbamate;
and the like.

The formulations provided by this invention can be prepared in any of a number of ways including dry mixing, spray drying, melt extrusion and the like. A preferred method of preparation comprises dissolving a suitable amount of the aforementioned copolymer in a solubilizing organic solvent that is readily removed by evaporation, and then adding the desired amount of pharmacologically active agent, followed by uniform mixing and subsequent removal of the organic solvent. For example, about 50 grams of a copolymer derived from about 80 weight percent of lactic acid and about 20 weight percent of glycolic acid, having an inherent viscosity of about 0.18 and molecular weight of about 25,000, can be dissolved in about 200 to about 400 ml. of a suitable organic solvent such as dichloromethane, acetone, dimethyl ether, tetrahydrofuran, chloroform, or the like. A pharmacologically active anthelmintic agent, such as fenbendazole, in the amount of about 50 g., is then added to the dissolved copolymer. The solution thus formed is stirred for uniform mixing and then the solvent is removed by evaporation, thus providing a uniformly mixed formulation of copolymer and active agent in a solid mass. The solid so formed can be ground to uniformity and encapsulated for convenient oral administration to an animal. For instance, the formulation can be administered orally to a range fed calf for effective control of parasites such as worms. Such treatment provides uniformly controlled release of anthelmintic agent to the animal, such that the effective dose of active ingredient is safe for the animal. Said effective dose typically amounts to less than about 500 mg. per animal each day. The novel formulation affords treatment to the animal for as long as about 10 to about 60 days, typically about 30 days.

The formulations of the invention can alternatively be prepared by first dissolving the copolymer and active agent in a suitable organic solvent, followed by removal of the solvent by evaporation, and then the copolymer-active agent formulation can be melted, for example by heating to about 130° C., and the melt can be extruded into rods having a diameter from about 1.0 to about 10.0 millimeters. The extruded rods can be cut to desired lengths so as to provide the desired specific amount of active agent. For example, a formulation which includes about 50 grams of fenbendazole and about 50 grams of a copolymer derived from about 70 to about 80 weight percent of lactic acid and about 30 to about 20 percent glycolic acid, said copolymer having an inherent viscosity of about 0.13 to about 0.23, can be melt extruded into rods having a diameter of about 4.0 mm. Such rods of formulated anthelmintic agent are, when cooled to room temperature, quite hard and brittle, thereby easily cut, and if desired, ground to uniformity. Such rods can be cut into desired lengths so as to obtain the desired dose of active ingredient. For example, an extruded rod of about 20 to 30 inches can be cut and ground into small particles and passed through an appropriate wire sieve, for example from about 60 to about 160 mesh, so as to obtain formulated copolymer anthelmintic agent that is easily encapsulated. Alternatively, the rods thus formed can be cut into sections of about 2 to 6 inches in length and orally administered to an animal.

The formulations provided by this invention can contain, in addition to the copolymer matrix and the active ingredient, other substances commonly utilized in medicinal formulations. Diluents, carriers, binders, excipients and adjuvants routinely incorporated in such formulations include gum tragacanth, acacia, corn starch, gelatin, alginic acid, magnesium stearate, aluminum monostearate, span 80, tween 80, sorbitan monostearate, hexaglyceryldistearate, glyceryldistarate, sucrose, lactose, methylparabene, propylparaben, beeswax, mannitol, propylene glycol, microcrystalline, cellulose, calcium silicate, silica, polyvinylpyrrolidone, cetostearyl alcohol, cocoa butter, polyoxyethylene sorbitan monolaurate, ethyl lactate, sorbitan trioleate, calcium stearate, talc and the like.

It will of course be recognized that the particular oral dose of formulated active ingredient will be determined in part by considerations such as the animal to be treated, the particular parasites to be treated or guarded against, whether the treatment required is therapeutic or prophylactic, the particular biological effects manifested by the active ingredient utilized in the formulation, and the extended period of time over which effective treatment and control is desired. In general, however, this invention contemplates that the typical amount of active ingredient employed in the formulations will be such that the daily payout of such active agent is sufficient to provide effective control to the host animal for a sufficiently prolonged period of time following a single administration. Typically, the dose of active ingredient, as formulated according to this invention, will be such that the daily payout of active ingredient will amount to about 0.2 to about 20 parts per million when analyzed in terms of blood concentration. Such blood level of active ingredient can be achieved by administering sufficient controlled release formulation so that the active ingredient administered amounts to about 0.1 to about 50 mg/kg of animal body weight. For example, an animal weighing about 500 kg can be given sufficient controlled release formulation so that the dose of active ingredient, such as methyl 5(6)phenylthio-2-benzimidazole carbamate (i.e. fenbendazole), will be about 0.5 to about 25 grams, ideally about 10 grams. The formulation thus administered will give uniform dosing to the animal for an extended period of time, such as about 30 days. If the active ingredient was indeed administered in the amount of 10 grams, the host animal would receive about 300 mg each day, for a daily dosage of active ingredient of about 0.6 mg/kg of animal body weight. Such dosage is ideally suited for the continuous control and treatment of parasitic infestation in ruminant animals such as cattle and sheep. The formulation is readily encapsulated, for example into an open ended steel cylinder, for convenient oral administration to the reticulo-rumen of the ruminant. The packed cylinder is of sufficient density to remain indefinitely in the reticulo-rumen portion of the ruminant's stomach, thus allowing the controlled release of active ingredient via the reticulo-rumen. A steel cylinder particularly suited to oral administration is described by Simpson in Ser. No. 74,683 filed Sept. 12, 1979.

The controlled release formulations provided by this invention are of particular importance in the treatment and control of endoparasites in cattle. The invention provides formulations and a method of treatment which is ideally suited to use in feed lots as well as to use in range fed animals.

As already pointed out, the active ingredients utilized in the controlled release formulations of this invention are either known in the art, or are readily preparable by art recognized methods. Most of the various classes of compounds utilized in the formulations have been extensively evaluated for their parasitic activity. A number of the compounds utilized in the formulations of this invention have been widely distributed in the marketplace. For example, a preferred benzimidazole, namely fenbendazole, i.e. methyl 5(6)phenylthio-2-benzimidazole carbamate, is currently in use as a drench and is known as Panacur. Similarly, levamisole, another preferred anthelmintic, is extensively used as a ruminant anthelmintic agent in the form of a drench, bolus, feed additive, and the like, and is marketed under names such as Tramisol, Nilverm and Levasol. Most of the available products are utilized as drenches or feed additives. These forms of administration are of course not applicable to prolonged treatment. The use of all of such agents is greatly enhanced by the controlled release formulations provided by this invention.

The controlled and continuous release of active ingredient from the formulations provided by this invention has been demonstrated in a number of in vivo experiments. One such evaluation involved the controlled release formulation comprised of a copolymer derived from about 80 weight percent of lactic acid and about 20 weight percent of glycolic acid, having a viscosity of about 0.20 and about 50 weight percent fenbendazole uniformly dispersed throughout. (Designated Formulation A in Table I). A second formulation was evaluated which comprised a copolymer derived from about 80 weight percent of lactic acid and about 20 weight percent of glycolic acid, having a viscosity of about 0.17 and about 50 weight percent fenbendazole. (Designated Formulation B in Table I.) Formulation B was also tested using about 50 weight percent fenbendazole, about 48 weight percent of the copolymer of formulation B, and about 2 weight percent sodium lauryl sulfate. (Designated Formulation C in Table I.) In one such study, mature cattle were equipped with a fistula for ready access to the reticulo-rumen portion of the stomach. Preweighed steel boluses containing formulations as described above were placed, via the fistula, into the rumen of each of six heifers. The animals were permitted to graze as desired, and were allowed to drink water freely. The formulation filled bolus was removed from the animals, via the fistula, at 13 day intervals over about a one month test period. Each bolus was weighed to determine the amount of active ingredient which had been administered to each animal, and then each bolus was returned to the reticulo-rumen via the fistula. The payout of active ingredient to each of the six test animals is given in Table I.

TABLE I

| Payout of Fenbendazole from formulations placed in the rumen of fistulated cattle. | | | | | |
|---|---|---|---|---|---|
| | Estimated Fenbendazole payout mg/head/day (weight loss of the bolus divided by 2) | | | | |
| Payout | Formulation A | | Formulation B | | Formulation C |
| Periods (days) | Animal #1 | Animal #2 | Animal #3 | Animal #4 | Animal #5 | Animal #6 |
| 0-14 | 110 | 341 | 113 | 103 | 69 | 108 |
| 14-28 | 504 | 786 | 575 | 596 | 421 | 421 |

According to the data presented in Table I, the average daily payout of fenbendazole, from a formulation of this invention containing 50 weight percent of fenbendazole, is about 307 mg/head/day for animal #1, about 564 mg/head/day for animal #2, about 344 mg/head/day for animal #3, about 350 mg/head/day for animal #4, about 245 mg/head/day for animal #5, and about 265 mg/head/day for animal #6. The average daily payout for all six animals is about 349 mg/head/day.

When the above described in vivo experiment on fistulated cattle was repeated using a controlled release formulation comprised of a copolymer derived from about 80 weight percent of lactic acid and about 20 weight percent of glycolic acid, having a viscosity of about 0.20 dl/g. and about 25 weight percent fenbendazole uniformly dispersed throughout, the payout of active ingredient to each of two test animals is given in Table II.

TABLE II

Payout of Fenbendazole from formulations placed in the rumen of fistulated cattle.

| Payout Periods (days) | Estimated Fenbendazole payout mg/head/day (averaged) | |
|---|---|---|
| | Animal #1 | Animal #2 |
| 0–14 | 41 | 25 |
| 15–28 | 55 | 63 |
| 29–42 | 80 | 84 |
| 43–56 | 91 | 96 |
| 57–70 | 93 | 102 |

Once all of the formulation contained in the steel capsule has been released, the empty capsule is of such weight that it simply remains in the reticulorumen. Additional filled capsules can be administered as needed, and all such capsules can be removed at the time of slaughter. Such removed capsules can be cleaned and repacked with the same or different formulation and re-administered to ruminant animals, thereby adding economical benefits to the present invention.

As hereinabove mentioned, this invention comprehends a method of controlled prolonged treatment of domestic animals suffering from internal parasitic infestation and in need of treatment or suspected of being susceptible to parasitic infestation comprising administering an effective dose of a controlled release parasitic formulation which is comprised of about 20 to about 80 percent by weight of a parasitic agent intimately dispersed throughout about 80 to about 20 percent by weight of a copolymeric matrix derived from the condensation of about 60 to about 95 weight percent of lactic acid and about 40 to about 5 weight percent of glycolic acid, said copolymer having an inherent viscosity of about 0.08 to about 0.30 when measured in chloroform, and a molecular weigh of about 6000 to about 35000. The method is preferably carried out by administering a formulation comprised of about 30 to about 70 percent by weight of an anthelmintic agent dispersed throughout a copolymer derived from about 70 to about 80 weight percent lactic acid and about 30 to about 20 weight percent glycolic acid, with an inherent viscosity of about 0.13 to about 0.23 and a molecular weight of about 15000 to about 30000. The method also is preferably carried out utilizing controlled release formulations wherein the anthelmintic agent is selected from benzimidazoles, particularly benzimidazole carbamates, and related commonly used anthelmintic agents. Especially preferred anthelmintic agents to be used in the form of controlled release formulations according to this invention include methyl 5-benzoyl-2-benzimidazole carbamate, methyl 5(6)-(phenylthio)-2-benzimidazole carbamate, methyl 5-phenylsulfinyl-2-benzimidazole carbamate, 5-[(cyclopropylmethyl)sulfinyl]-1H-benzimidazole-2-yl carbamate, methyl 5-propylthio-1H-benzimidazole-2-yl carbamate, as well as related parasitic agents such as levamisole, albendazole, cambendazole, parbendazole, thiabendazole, oxibendazole, oxfendazole, flubendazole, closantel, morantel, and related anthelmintic agents.

The method of the invention will be practiced by administering a controlled release formulation of the invention containing sufficient active agent such that the daily payout is an effective amount for the control and prevention of endoparasitic infestation. The particular dose to be administered will be determined in part by the particular parasitic agent to be utilized in the controlled release formulation, as well as the particular ratio of active ingredient to copolymeric matrix, the route of administration, as well as the host animal to be treated and the parasite to be guarded against. Typically, the dose will be such that the blood concentration of parasitic agent is maintained at a level which provides effective control with no substantial adverse side effects. Such concentration will generally amount to about 0.2 to about 20.0 parts per million.

The method provided herein contemplates administering the controlled release formulations by the route generally recognized as effective for the particular parasitic agent utilized. Such methods include oral and parenteral administration. The formulations can be suspended in a suitable vehicle such as sesame oil for conveniant subcutaneous or intramusular administration, or alternatively can be implanted. The method provides for the control of parasitic infestation in animals for about ten to about sixty days following a single administration, and longer periods of treatment can be achieved by repeated administration as desired.

In an effort to more fully describe the product of this invention, the following detailed examples are provided by way of illustration.

EXAMPLE 1

Preparation of Copolymer matrix

To a 3-neck round bottom flask equipped with a condenser and thermometer were added 355.0 g. of lactic acid, 145.0 g. of glycolic acid and 5.0 g. of Dowex HCR-W2-H ion-exchange resin. The mixture was stirred and heated to 130° C. for three hours, during which time 200 ml. of water were distilled and collected. After discarding the water thus produced, stirring and heating were continued and the pressure was gradually reduced by vacuum over three hours, after which time the temperature of the reaction mixture had increased to 150° C. at a final pressure of 5 torr. An additional 5.0 g. of Dowex HCR-W2-H catalyst was added to the reaction mixture, and the mixture then was heated to 170° C. at 5.0 torr for twenty-four hours, and then at 185° C. at 5.0 torr for an additional 48 hours. The molten reaction mixture next was filtered to remove most of the ion exchange polymerization catalyst, and the filtrate was allowed to cool to room temperature to give 300 g. of 65 percent lactic—35 percent glycolic copolymer. The copolymer was analyzed by proton nuclear magnetic resonance spectrometry and shown to be comprised of 65 percent by weight of lactic units and 35 percent glycolic units.

The viscosity of the copolymer was determined in a Ubbelohde viscometer in which chloroform had an efflux time of 51 seconds at 25° C. The copolymer was dissolved in chloroform at a concentration of 0.50 g. per 100 ml. of solvent. Inherent viscosity of the copolymer was then determined according to the formulas:

$$\eta rd = \frac{t}{t_o} \quad \eta inh = \frac{\ln \eta rel}{C}$$

wherein:
ηrel=relative viscosity
$t_o$=efflux time of solvent (CHCl$_3$)
t=efflux time of solution
ηinh=inherent viscosity
C=conc. in grams/100 ml.

The inherent viscosity of the copolymer thus prepared was determined to be 0.19 dl/g.

EXAMPLE 2

Following the general procedure set forth in Example 1, 710 g. of lactic acid and 290 g. of glycolic acid were condensed in the presence of a total of 40.0 g. of Amberlyst 15 ion exchange polymerization catalyst to afford 600 g. of a copolymer comprised of about 70 percent lactic units and about 30 percent glycolic units. The copolymer had the following viscosity: 0.18 dl/g.

EXAMPLE 3

Following the general procedure of Example 1, 355.0 g. of lactic acid were condensed with 145.0 g. of glycolic acid in the presence of a total of 10.0 g. of Amberlyst 15 ion-exchange polymerization catalyst. After removing the catalyst by filtration of the molten reaction mixture, there was provided 300 g. of a copolymer derived from about 70 percent by weight of lactic acid and about 30 percent by weight of glycolic acid. The copolymer exhibited the following viscosity: 0.18 dl/g.

EXAMPLE 4

Following the general procedure of Example 1, 1080 g. of lactic acid were condensed with 252 g. of glycolic acid in the presence of a total of 25.0 g. of Dowex HCR-W2-H ion-exchange polymerization catalyst to give, after removal of the catalyst, 750 g. of a copolymer which was shown by proton NMR to contain about 79 percent of lactic units and about 21 percent of glycolic units. The copolymer exhibited the following viscosity: 0.20 dl/g.

EXAMPLE 5

Following the procedure of Example 1, 432 g. of lactic acid were condensed with 101 g. of glycolic acid in the presence of a total of 5.0 g. of Dowex HCR-W2-H ion exchange polymerization catalyst to provide, after work-up, 300 g. of a copolymer derived from about 77 weight percent of lactic acid and about 23 weight percent of glycolic acid. The copolymer had a viscosity of 0.21 dl/g.

EXAMPLE 6

Following the procedure of Example 1, 432 g. of lactic acid were condensed with 101 g. of glycolic acid in the presence of a total of 2.5 g. of Dowex HCR-W2-H ion-exchange polymerization catalyst to provide 300 g. of a copolymer comprised of about 76 percent lactic units and about 24 percent glycolic units. The copolymer had the following viscosities:

0.12 after 24 hours at 170° C.
0.20 after 24 hours at 185° C.
0.23 after 40 hours at 185° C.

EXAMPLE 7

The procedure of Example 1 was followed to condense 1080 g. of lactic acid with 120 g. of glycolic acid in the presence of a total of 25.0 g. of Dowex HCR-W2-H ion exchange polymerization catalyst. After workup, there was recovered 750 g. of a copolymer derived of about 89 weight percent of lactic acid and about 11 weight percent of glycolic acid having the following viscosity: 0.20 dl/g.

The copolymers required for the formulations provided by this invention additionally have been characterized by gel permeation chromatography (high pressure liquid chromatography) and subsequent determination of molecular weight. Gel permeation chromatography separates sample molecules by differences in effective molecular size in solution. Separation is accomplished as a result of the pore size distribution in the packing material. This analytical technique allows determinations of weight-average molecular weight, number average molecular weight, molecular weight distribution, and dispersity for polymeric materials.

Several such experiments have been carried out on the copolymers required by this invention. Standard gel permeation chromatographic columns were used, and the support in each case was commercial μStyragel. All samples and standards were dissolved in a solution of 80 parts tetrahydrofuran and 20 parts dichloromethane. The indirect method (i.e. the "Q-Factor Method") of calibrating the gel permeation chromatographic columns was used to obtain molecular weight averages for the copolymers. Commercial polystyrene, with a Q Factor of 41.3, was used in the calibrations. The following Table presents several determinations of molecular weight by standard gel permeation chromatographic techniques as outlined above. A more detailed discussion of the technique utilized is presented by Slade in *Polymer Molecular Weights*, Marcel Dekker, Inc., 1975.

In the Table, column I presents the relative proportions of lactic units and glycolic units making up the copolymer analyzed. Column II gives the inherent viscosity of each copolymer analyzed. Column III reports the strong acid ion exchange resin utilized to prepare the copolymer being analyzed. Column IV presents the weight average angstrom size as determined from the gel permeation chromatographic retention time for the particular copolymer. Column V presents the weight average molecular weights for the various copolymers prepared by the process of this invention. The weight average molecular weights are determined by multiplying the Q-Factor for polystyrene (41.3) times the weight average angstrom size for the particular copolymer being analyzed.

As demonstrated in the Table, the preferred copolymers of this invention have a molecular weight from about 15,000 to about 35,000, and ideally from about 15,000 to about 30,000.

| Column I | Table of Weight Average Molecular Weights | | | |
|---|---|---|---|---|
| | II | III | IV | V |
| 80:20 | 0.18 | Amberlyst 15 | 412.3 | 17,027 |
| 80:20 | 0.19 | Dowex HCR-W2-H | 454.2 | 17,862 |
| 80:20 | 0.19 | Dowex HCR-W2-H | 819.3 | 33,837 |
| 90:10 | 0.20 | Dowex HCR-W2-H | 749.3 | 30,946 |

-continued

Table of Weight Average Molecular Weights

| Column I | II | III | IV | V |
|---|---|---|---|---|
| 90:10 | 0.17 | Amberlyst 15 | 580.0 | 23,954 |
| 90:10 | 0.21 | Dowex HCR-W2-H | 841.5 | 34,754 |
| 70:30 | 0.12 | Dowex HCR-W2-H | 400.5 | 16,541 |
| 70:30 | 0.14 | Dowex HCR-W2-H | 299.8 | 12,382 |
| 70:30 | 0.15 | Dowex HCR-W2-H | 367.1 | 15,161 |
| 75:25 | 0.12 | Dowex HCR-W2-H | 349.2 | 14,422 |
| 75:25 | 0.19 | Dowex HCR-W2-H | 505.9 | 20,894 |

EXAMPLE 8

Formulation for control of endoparasites in ruminants

A uniform dry mixture made up of 200 grams of methyl 5(6)-(phenylthio)benzimidazole carbamate, i.e. fenbendazole, and 200 grams of a copolymer derived from about 80 weight percent lactic acid and about 20 weight percent of glycolic acid, said copolymer having an inherent viscosity of about 0.18, is heated to about 90° C. The heated mixture is extruded at that temperature through a standard killion extruder, and the extended product is packed into steel capsules measuring 35 mm×50 mm and weighing about 100 grams when empty. Each capsule will contain about 40 grams of the formulation, thus containing about 20 grams of active ingredient. Such steel capsules containing the controlled release formulation of fenbendazole can be administered to ruminant calves weighing about 500 kg for the prolonged treatment and control of intestinal parasites. The steel capsule thus administered is of sufficient weight that it is retained in the reticulo-rumen portion of the ruminant's stomach. The formulation thus administered is effective for providing controlled and continuous release of active ingredient to such animal for a period of about ten to about sixty days, so that the average daily dose of active ingredient is about 0.5 to about 1.0 mg/kg of animal body weight.

EXAMPLE 9

Controlled release formulation of 6-aminophenyl(2,3,5,6) tetrahydroimidazo(2,1-b)thiazole (levamisole)

A solution containing 15 g. of a copolymer derived from 70 percent by weight of lactric acid and 30 percent of glycolic acid (viscosity 0.12), and 5 g. of levamisole in 80 ml. of dichloromethane was spray dried. The inlet temperature was about 48° C. and the outlet temperature was about 27 to about 30° C. The feed rate was 7 ml. per minute with a pressure of 1 psc. The spray dried product was a white powder which contained 25% by weight of active ingredient (levamisole) and was ideally suited to subcutaneous injection in sesame oil for the effective prolonged treatment of parasites.

EXAMPLE 10

Controlled release formulation of methyl-5-propylthio-1H-benzimidazole-2-yl carbamate (albendazole)

A solution of 14.25 g. of a copolymer derived from the condensation of 70 weight percent of lactric acid and 30 weight percent glycolic acid (viscosity 0.12 dl/g) dissolved in 76 ml. of dichloromethane containing 4.75 g. of albendazole was spray dried. The inlet temperature was about 48° to about 50° C. and the outlet temperature was about 28° C. The nozzel pressure was 1 psi and the feed rate was 16 ml/min. The spray dried formulation was passed through a size 60 mesh screen to give 12.7 g. of controlled release formulation of albendazole. The formulation was suspended in sesame oil for convenient subcutaneous injection for the control of parasitic infestation.

EXAMPLE 11

Controlled Release Dormulation of 6-(1,4-Cyclohexadien-1-yl)-2,3,5,6-tetrahydroimidazo[2,1-b]thiazole A solution of 10 g. of 6-(1,4-cyclohexadien-1-yl)-2,3,5,6-tetrahydroimidazo[2,1-b]thiazole (U.S. Pat. No. 4,104,400) in 100 ml. of acetone containing 10 g. of a copolymer derived from the condensation of about 80 weight percent of lactic acid and about 20 weight percent of glycolic acid is spray dried to give a solid powder. The powder so formed is suspended in sesame oil and injected into animals at the dose of about 20 mg/kg for the effective systemic control of liver flukes and the like.

EXAMPLE 12

Controlled Release Formulation of methyl 5-[(cyclopropylmethyl)sulfinyl]-1H-benzimidazol-2-yl carbamate A solution of 10.0 g. of methyl-5-[(cyclopropylmethyl)sulfinyl]-1H-benzimidazol-2-yl carbamate was dissolved in a solution of 100 ml. of acetone containing 10.0 g. of a copolymer derived from the condensation of 80 weight percent of lactic acid and 20 weight percent glycolic acid (molecular weight about 25000). The solution was spray dried to provide a uniformly mixed solid. The solid was suspended in 50 ml. of sesame oil containing 0.5 g. of beeswax and 0.5 g. of aluminum monostearate.

I claim:

1. A controlled release biodegradable dosage form useful in the prolonged therapeutic and prophylactic control of endoparasites in domestic animals comprising about 20 to about 80 percent by weight of a anthelmintic agent initimately dispersed throughout about 80 to 20 percent by weight of a copolymeric matrix derived from the condensation of about 60 to about 95 weight percent of lactic acid and about 40 to about 5 weight percent of glycolic acid, said copolymer having an inherent viscosity of about 0.08 to about 0.30 when measured in chloroform, and a molecular weight of about 6000 to about 35000, said copolymer being substantially free of polymerization catalyst.

2. The formulation of claim 1 wherein the anthelmintic agent is present in the amount of about 30 to about 70 percent by weight, and the copolymer matrix is derived from about 60 to about 90 percent lactric acid and about 40 to about 10 percent glycolic acid, with an inherent viscosity of about 0.10 to about 0.25.

3. The formulation of claim 2 wherein the copolymeric matrix is derived from about 70 to about 80 percent by weight of lactic acid and about 30 to about 20 percent by weight of glycolic acid, with an inherent viscosity of about 0.13 to about 0.23 and a molecular weight of about 15000 to about 30000.

4. The formulation of claim 1 wherein the anthelmintic agent is a benzimidazole of the formula

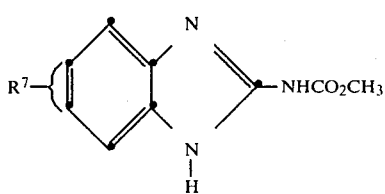

wherein: $R^7$ is hydrogen, lower alkyl, lower alkoxy, lower alkylthio, benzoyl, halobenzoyl, phenylthio, phenylsulfinyl, cyclopropylmethylsulfinyl, and lower alkyl—$CO_2NH$—.

5. The formulation of claim 4 wherein $R^7$ is phenylthio.

6. A method of controlled prolonged treatment of domestic animals suffering from endoparasitic infestation and in need of treatment or suspected of being susceptible to endoparasitic infestation comprising administering an effective dose of a controlled release anthelmintic formulation which is comprised of about 20 to about 80 percent by weight of an anthelmintic agent intimately dispersed throughout about 80 to about 20 percent by weight of a copolymeric matrix derived from the condensation of about 60 to about 95 weight percent of lactic acid and about 40 to about 5 weight percent of glycolic acid, said copolymer having an inherent viscosity of about 0.08 to about 0.30 when measured in chloroform, and a molecular weight of about 6000 to about 35000, said copolymer being substantially free of polymerization catalyst.

7. The method of claim 6 wherein the anthelmintic formulation comprises about 30 to about 70 percent by weight of a anthelmintic agent intimately dispersed throughout a copolymer which is derived from about 70 to about 80 weight percent of lactic acid and about 30 to about 20 weight percent of glycolic acid, said copolymer having a viscosity of about 0.13 to about 0.23 and a molecular weight of about 15000 to about 30000.

8. The method of claim 6 wherein the anthelmintic agent is a benzimidazole of the formula

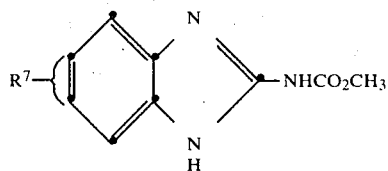

wherein: $R^7$ is hydrogen, lower alkyl, lower alkoxy, lower alkylthio, benzoyl, halobenzoyl, phenylthio, phenylsulfonyl, cyclopropylmethylsulfinyl, and lower alkyl—$CO_2NH$—.

9. The method of claim 8 wherein $R^7$ is phenylthio.

* * * * *